(12) United States Patent
McAlister et al.

(10) Patent No.: US 9,960,027 B2
(45) Date of Patent: May 1, 2018

(54) ANALYZING A COMPLEX SAMPLE BY MS/MS USING ISOTOPICALLY-LABELED STANDARDS

(71) Applicant: Thermo Finnigan LLC, San Jose, CA (US)

(72) Inventors: Graeme C. McAlister, San Jose, CA (US); Shannon Eliuk Dixon, San Jose, CA (US); Romain M. Huguet, San Jose, CA (US)

(73) Assignee: Thermo Finnigan LLC, San Jose, CA (US)

( * ) Notice: Subject to any disclaimer, the term of this patent is extended or adjusted under 35 U.S.C. 154(b) by 0 days. days.

(21) Appl. No.: 15/164,113

(22) Filed: May 25, 2016

(65) Prior Publication Data

US 2017/0345632 A1   Nov. 30, 2017

(51) Int. Cl.
*H01J 49/00*   (2006.01)
*H01J 49/42*   (2006.01)
(Continued)

(52) U.S. Cl.
CPC ...... *H01J 49/0072* (2013.01); *G01N 30/7233* (2013.01); *G01N 33/6848* (2013.01);
(Continued)

(58) Field of Classification Search
CPC .............. H01J 49/0072; H01J 49/0031; H01J 49/4215; H01J 49/425; G01N 30/7233; G01N 33/6848; G01N 2570/00
(Continued)

(56) References Cited

U.S. PATENT DOCUMENTS 7,529,629 B2 * 5/2009 Wang ............... G06F 19/703
 435/4
2003/0139885 A1 7/2003 Brock et al.
(Continued)

FOREIGN PATENT DOCUMENTS

WO   2008/142579 A2   11/2008

OTHER PUBLICATIONS

Liao et al., IsoQuant: A Software Tool for SILAC-Based Mass Spectrometry Quantitation. Analytical chemistry 84.10 (2012): 4535-4543. PMC. Web. May 18, 2017.*
(Continued)

*Primary Examiner* — Nicole Ippolito
*Assistant Examiner* — Hanway Chang
(74) *Attorney, Agent, or Firm* — Charles B. Katz

(57) ABSTRACT

A method and corresponding apparatus are disclosed for analysis of a peptide-containing sample. The sample is prepared by adding isotopically-labeled peptides corresponding to endogenous peptides of interest, and the prepared sample is analyzed by liquid chromatography-mass spectrometry (LCMS). Detection in a high-resolution, accurate mass (HRAM) MS1 spectrum of a precursor ion matching an isotopically-labeled peptide triggers acquisition of an MS/MS spectrum (preferably acquired in an ion trap or other fast mass analyzer) to determine if a product ion is present matching a characteristic product ion (e.g., the $y_1$ ion) of the isotopically-labeled peptide. If the characteristic product ion is present, then a HRAM MS/MS spectrum is acquired for detection and quantitation of the corresponding endogenous peptide.

16 Claims, 4 Drawing Sheets

(51) Int. Cl.
*G01N 30/72* (2006.01)
*G01N 33/68* (2006.01)

(52) U.S. Cl.
CPC ........ *H01J 49/0031* (2013.01); *H01J 49/425* (2013.01); *H01J 49/4215* (2013.01); *G01N 2570/00* (2013.01)

(58) Field of Classification Search
USPC ........................................ 250/281, 282, 288
See application file for complete search history.

(56) References Cited

U.S. PATENT DOCUMENTS

| | | |
|---|---|---|
| 2005/0063864 A1 | 3/2005 | Sano et al. |
| 2010/0279382 A1 | 11/2010 | Aebersold et al. |
| 2013/0214151 A1 | 8/2013 | Soldin |
| 2014/0051113 A1 | 2/2014 | Stephenson, Jr. et al. |

OTHER PUBLICATIONS

Gallien, et al., "Large-Scale Targeted Proteomics Using Internal Standard Triggered-Parallel Reaction Monitoring (IS-PRM)", Mol. Cell. Proteomics 2015, 14.6, pp. 1630-1644.

Yan, et al., "Index-ion Triggered MS2 Ion Quantification: A Novel Proteomics Approach for Reproducible Detection and Quantification of Targeted Proteins in Complex Mixtures", Mol. Cell. Proteomics 2011, 10 (3): M110.005611, pp. 1-15.

* cited by examiner

| Peptide No. | Peptide sequence | Charge | Precursor m/z | Product ($y_1$) m/z |
|---|---|---|---|---|
| 1 | SSAAPPPPPR* | +2 | 493.7683 | 185.1 |
| 2 | GISNEGQNASIK* | +2 | 613.3167 | 155.1 |
| 3 | HVLTSIGEK* | +2 | 496.2867 | 155.1 |
| 4 | DIPVPKPK* | +2 | 451.2834 | 155.1 |
| 5 | IGDYAGIK* | +2 | 422.7363 | 155.1 |

ANALYZING A COMPLEX SAMPLE BY MS/MS USING ISOTOPICALLY-LABELED STANDARDS

FIELD OF THE INVENTION

The present invention relates to mass spectrometry, and more particularly to targeted methods of analyzing a complex sample by MS/MS analysis using isotopically labeled standards.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 20091US1-NAT_ST25.txt, a creation date of Aug. 12, 2016, and a size of 2.73 KB. The sequence listing filed via EFS-Web is part of the specification and is hereby incorporated in its entirety by reference herein.

BACKGROUND OF THE INVENTION

Protein analysis by mass spectrometry is largely done via a bottom-up, data-dependent method. With this approach, proteins are first digested by enzymes into peptides. These peptides are then separated either by one or more dimensions of liquid chromatography. Following separation, the eluting peptides are ionized and analyzed with the mass spectrometer using an MS1 "survey scan". From this initial mass spectral analysis, precursors are selected for subsequent analysis using a set of criteria (e.g., precursor charge state). These selected precursors are further interrogated by MS/MS analysis (e.g., via isolation, fragmentation, and m/z analysis).

This approach is quite effective at covering a very wide range of peptides in a very short amount of time. However, due to the limited dynamic range of the MS1 analysis, and the stochastic nature of data-dependent precursor sampling, the depth and reproducibility of this approach is often poor. For example, it is rare that this approach provides complete coverage of biological functional groups or pathways (e.g., it is unlikely a data-dependent analysis would cover all the human kinases). These workflow limitations often result in poor overlap between replicate experiments.

Targeted proteomics approaches, such as selected reaction monitoring (SRM), multiple reaction monitoring (MRM), and parallel reaction monitoring (PRM), are the traditional alternatives to the data-dependent approach. In lieu of selecting precursors from an MS1 survey spectrum, the instrument dwells upon select m/z regions that are informed by a list that is populated by the user before the analysis. That is, the instrument continuously collects MS/MS spectra, independent of whether there is any detectable signal in an MS1 spectrum. By specifically dwelling on prespecified precursors, these methods are capable of much higher sensitivity and reproducibility than the data-dependent workflow.

However, one of the main compromises with these targeted analyses is breadth. Dwelling upon low abundance precursors comes at the cost of interrogating higher abundance species. Also, without any pre-screening of the eluting peptides (i.e., MS1 survey spectra), it is expected that some portion of the targeted MS/MS analyses will occur when there is no precursor present (i.e., MS/MS spectra will be collected while the precursor isn't eluting). These concerns can be somewhat mitigated by employing complex retention time scheduling—that is, along with the list of precursor targets the user provides a list of retention times. However, scheduling targeted scans in this manner requires precise knowledge of peptide retention times. These times are specific to the chromatographic setup, and the utility of these times are heavily contingent upon the reproducibility of the chromatographic separation.

As an alternative to these traditional approaches, two labs have published workflows that attempt to realize the depth and reproducibility of the targeted workflow while still leveraging the ease of use of the data-dependent approach (see Gallien et al., "Large-Scale Targeted Proteomics Using Internal Standard Triggered-Parallel Reaction Monitoring (IS-PRM)", Mol. Cell. Proteomics, Vol. 14, No. 6, pp. 1630-44 (2015); Yan et al., "Index-ion Triggered MS2 Ion Quantification: A Novel Proteomics Approach for Reproducible Detection and Quantification of Targeted Proteins in Complex Mixtures", Mol. Cell. Proteomics, Vol. 10, No. 3, M110.005611 (2011)). These workflows begin with the addition of heavy peptide standards to the analytical sample. These heavy standards have sequences that are analogous to endogenous peptides of interest. By incorporating specific heavy isotopes, these standards differ in mass from the endogenous form of the peptide; however, their retention times match exactly. In the published workflows, the mass spectrometer method includes low-quality targeted scans on the spiked-in standards. Following acquisition of the targeted MS/MS transitions/spectra, the data is analyzed, and if certain conditions are met the instrument triggers a high-quality MS/MS analysis on the expected location of the endogenous form of the peptide.

While these workflows have been partially successful at addressing the limitations and disadvantages of the established data-dependent and targeted methods, they tend to have a steep tradeoff between sensitivity and selectivity, with one of the published workflows offering good sensitivity but limited selectivity, and the other exhibiting excellent selectivity with modest sensitivity. Furthermore, both workflows rely on retention time scheduling to achieve acceptable duty cycle and selectivity, which increases method setup complexity, places stress on sample availability, and can compromise robustness, particularly where run-to-run variation of chromatographic separation exits.

SUMMARY

Roughly described, embodiments of the present invention adopt an approach in which detection of a characteristic product ion derived from dissociation of an isotopically-labeled peptide ion triggers MS/MS analysis of the corresponding endogenous peptide ion. More specifically, a method is provided for analysis of a peptide-containing sample wherein the sample is spiked with a plurality of isotopically-labeled peptides, at least some of which are labeled forms of endogenous peptides of interest. According to one example, the labeled peptides are metabolically labeled with heavy forms of the C-terminal lysine or arginine. The sample is subjected to chromatographic separation and the eluting components are analyzed by mass spectrometry according to a prescribed sequence of steps. An MS1 survey scan is performed, preferably in a high-resolution mass analyzer such as an orbital electrostatic trap, and the resultant MS1 spectrum is processed to identify precursor ions in the spectrum that have mass-to-charge ratios (m/z) that match an m/z that corresponds to one of the isotopically-labeled peptides. If a match is identified, then a first MS/MS scan is performed to acquire a spectrum of product ions generated by dissociation of the matching precursor ion appearing in the MS1 spectrum. In order to provide high sensitivity and throughput, the first MS/MS scan may be performed in a fast and sensitive mass analyzer, such as a quadrupole ion trap. The speed of the first MS/MS scan may be increased by limiting the scan range to a narrow m/z window around the value of a characteristic product ion of the isotopically labeled peptide, for example the $y_1$ product ion. If the MS/MS spectrum exhibits a peak of sufficient intensity (indicating with a high degree of confidence the presence of the characteristic product ion of the isotopically-labeled peptide), then one or a series of MS/MS scans are performed to quantify the endogenous peptide ion corresponding to the labeled peptide ion. The MS/MS scan of the endogenous peptide may be conducted in the high-resolution (e.g., orbital electrostatic trap) mass analyzer.

The foregoing method presents several advantages relative to the prior art approaches described above, including achieving very good selectivity while retaining high sensitivity, and avoiding the need for retention-time scheduling and/or other techniques that complicate method development and render the method vulnerable to problems arising from run-to-run variations.

BRIEF DESCRIPTION OF THE DRAWINGS

In the accompanying drawings:

FIG. 3 is a table containing an inclusion list of m/z values of labeled peptide ions, used for matching of precursor ions appearing in an MS spectrum.

DETAILED DESCRIPTION OF EMBODIMENTS

Figure 1:
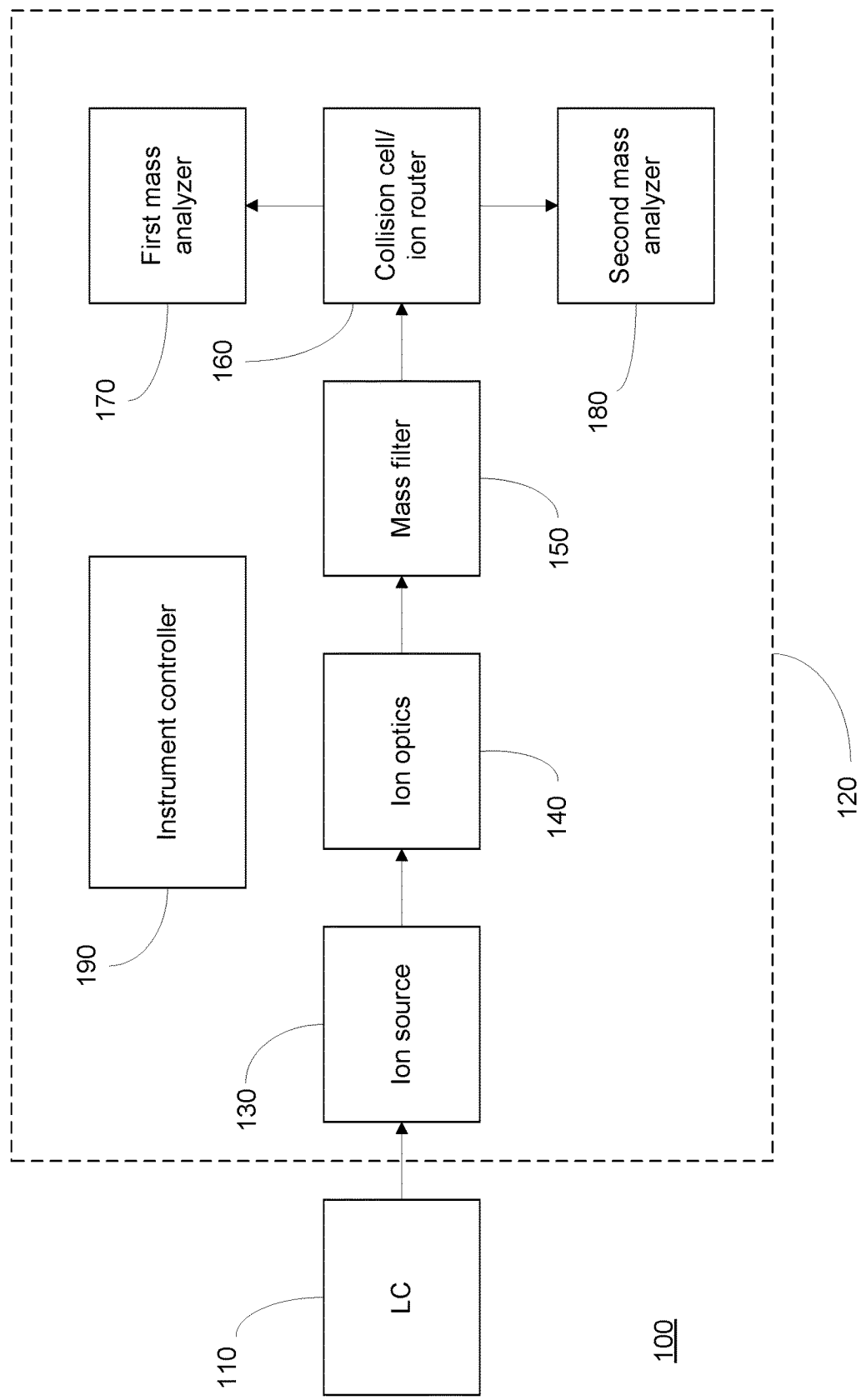
FIG. 1 is a symbolic diagram depicting a liquid chromatography/mass spectrometry (LC/MS) system configurable to perform analysis of peptide-containing samples in accordance with embodiments of the present invention.

FIG. 1 depicts an LC/MS system 100 that may be employed to implement embodiments of the present invention. The description of LC/MS system 100 is intended to be illustrative of an exemplary implementation, and should not be construed as limiting the invention to any particular instrument architecture. LC/MS system 100 includes a liquid chromatography (LC) system 110 coupled to a mass spectrometer 120. LC system 110 may be conventionally provided with pumps for loading the sample onto a chromatographic column and for directing one or more solvents onto the column according to an elution gradient to cause components of the sample to be chromatographically separated, such that they are eluted from the column at different retention times. The eluate from LC system 110 is passed to an ionization source 130 of mass spectrometer 120, which produced gas-phase ions from molecules, including biological molecules such as peptides, contained in the sample. The ionization source may be of any suitable type known in the art, such as an electrospray ionization (ESI) source. The ions produced in source 130 are delivered via ion optics 140 (which will typically include some combination of ion lenses and ion guides designed to confine and focus the ions to an ion path axis) to a quadrupole mass filter (QMF) 150, which is operable, by adjustment of the amplitudes of oscillatory and resolving direct current (DC) voltage applied to its electrodes, to selectively transmit only ions within a desired range of mass-to-charge (m/z) values. The ions thus transmitted (which may comprise a single ion species or multiple ion species) are passed into a gas-filled collision cell 160, where the ions may undergo collisions with atoms or molecules of gas resulting in fragmentation into product ions via collisionally activated dissociation (CAD). Collision cell 160 may also function to route ions transmitted thereto and/or formed therein by CAD to a selected one of the first mass analyzer 170 or second mass analyzer 180. In one example of mass spectrometer 120, first mass analyzer 170 is an orbital electrostatic trap mass analyzer (e.g., a mass analyzer of the type sold by Thermo Fisher Scientific Inc. under the trademark "Orbitrap"), and second mass analyzer 180 is a quadrupole ion trap (e.g., a two-dimensional orthogonal-ejection ion trap). Each mass analyzer functions to separate ions according to their m/z's such that a mass spectrum may be acquired. The various components of mass spectrometer 150 communicate with and are controlled by controller 190, which also serves to record and process mass spectral data generated by the mass analyzers. Although controller 190 is depicted symbolically as a single unit, its functions will typically be distributed across a number of physically separate devices, including but not limited to specialized processors, storage, memory, general-purpose computers and application-specific circuitry. Controller 190 is adapted with a user interface, enabling the user to specify experimental parameters or other information, and to view and manipulate results. Controller 190 is further configured with executable instructions, typically in the form of software code, for performing certain of the steps of the methods described below.

Figure 2:
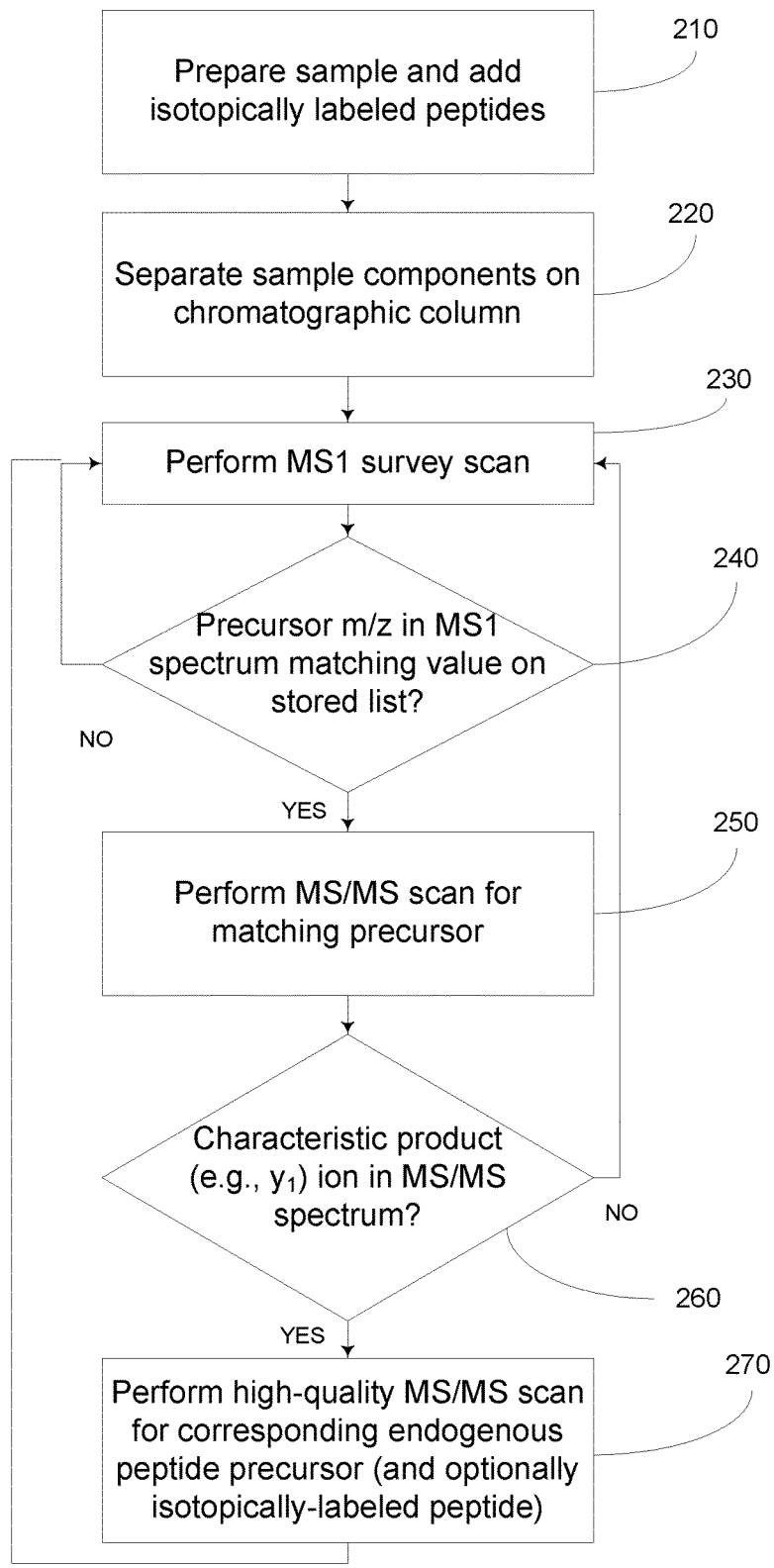
FIG. 2 is a flowchart depicting steps of a method for analysis of peptide-containing samples by mass spectrometry.

The steps of a method for analyzing peptide-containing samples in accordance with embodiments of the present invention may be understood with reference to the FIG. 2 flowchart. The method includes an initial step 210 of preparing a "spiked" sample that incorporates one or more isotopically-labeled ("heavy") peptides corresponding to targeted endogenous peptides. Typically, the sample will take the form of a biological fluid (e.g., blood plasma, saliva, urine, cerebrospinal fluid) or tissue extract. The sample may be subjected to one or more preparation steps known in the art, either prior to or following enzymatic digestion, to remove unwanted components, concentrate or purify components of interest, and to facilitate analysis by LC/MS. According to the approach commonly known as "bottom-up" analysis, proteins contained in the sample may be digested to form peptides by the addition of a proteolytic enzyme, such as trypsin.

Following or concurrently with other sample preparation steps, a set of isotopically-labeled peptides are added in known quantities to the sample. At least some of the added isotopically-labeled peptides are labeled versions of the endogenous peptides of interest (i.e., those to be detected and quantified in the sample). In one example, if the endogenous peptides present in the sample are tryptic peptides (noting that trypsin cleaves proteins next to arginine (R) or lysine (K)), then the isotopically-labeled peptides may be metabolically labeled with heavy forms of C-terminal arginine or lysine. For example, if it is desired to measure the amount of peptide IGDYAGIK (SEQ ID NO:1) in a sample, then the set of isotopically-labeled peptides added to the sample may include IGDYAGIK* (SEQ ID NO:2), where K* represents the heavy (fully $^{13}C$ and $^{15}N$ substituted) form of the terminal lysine amino acid, such that the isotopically-labeled version of the peptide has a mass 8 Dalton (Da) greater than the endogenous (light) peptide. In another example, the endogenous peptides of interest include SSAAPPPPPR (SEQ ID NO:3), and the isotopically-labeled peptides include SSAAPPPPPR* (SEQ ID NO:4), where R* is the fully $^{13}C$ and $^{15}N$ substituted form of the terminal arginine amino acid, yielding an isotopically-labeled version of the peptide having a mass 10 Da greater than the endogenous (light) peptide. This labeling scheme enables confirmation of the presence of a labeled peptide ion by detection of a characteristic product ion incorporating the labeled amino acid, such as the $y_1$ ion, as is discussed below.

It should be recognized that the present invention is not limited to the example presented above, in which the added standard consist of peptides having metabolically labeled terminal arginine or lysine. In alternative implementations of the invention, the labeled peptides may be metabolically labeled with heavy versions of other amino acids, or the labeled peptides may be labeled via a chemical tagging approach. Alternatively the sample of endogenous peptides may be labeled, while the spiked-in standard contains isotopes of natural abundances.

In another variant of the sample preparation method, isotopically-labeled intact proteins, corresponding to endogenous intact proteins of interest, are added to he sample prior to enzymatic digestion. The endogenous and isotopically-labeled proteins in the sample are then digested concurrently (e.g., by the addition of trypsin or other proteolytic enzyme) to yield endogenous and isotopically-labeled peptides, which serve as surrogates to the corresponding proteins, and may be analyzed in accordance with the mass spectrometry-based technique described below.

It is further noted that the labeling scheme utilized to produce the isotopically-labeled peptides should be selected in view of various performance factors relating to the mass spectrometry analysis method described below. More specifically, the method relies on the detection of characteristic product ions of the isotopically-labeled peptide to initiate quantitative measurement of the corresponding endogenous peptide. To improve specificity and avoid spurious triggering of quantitation scans, it is helpful to select an isotopic labeling scheme that will yield characteristic product ions from the labeled species that have m/z's sufficiently different from potentially interfering product ions generated by fragmentation of isobaric precursor ion species, e.g., precursor ions produced by ionization of peptides and other compounds that are not of interest.

The spiked sample, incorporating the isotopically-labeled peptides, is then chromatographically separated in step 220 into constituent components, e.g., by passing the spiked sample into a chromatographic column and gradually eluting components according to their hydrophobicities via a suitable elution gradient. The endogenous and labeled versions of a peptide have substantially identical hydrophobicities and elute from the column simultaneously. As the components elute from the column, they are passed to ionization source 130, which ionizes the sample components to form ions, including ions of the labeled peptides and corresponding endogenous peptides contained in the sample. The ions thus generated are then analyzed by mass spectrometry in accordance with the steps depicted in FIG. 2 and discussed below.

In step 230, an MS1 scan (also referred to as a "survey scan") is performed to acquire a mass spectrum of the precursor (intact) ions formed by ionization of the sample. In one embodiment, the MS1 scan is acquired in a mass analyzer, such as an orbital electrostatic trap mass analyzer, capable of acquiring high resolution/accurate mass (HRAM) spectral data, for example at a resolving power (at 200 m/z) exceeding 50,000 and at a mass accuracy better than 10 parts per million (ppm). The mass spectrum will typically include one or more peaks or features (referred to herein as precursor ion peaks) indicating the presence of ions at specific values of m/z. Each precursor peak will have a height or intensity that indicates the abundance of ions at the peak m/z. In certain implementations, the mass spectrum may be filtered to remove peaks that cannot be reliably distinguished from noise, e.g., by discarding peaks from the spectrum that do not meet a minimum intensity or signal-to-noise threshold.

The mass spectrum (or a filtered version thereof) is processed to compare m/z values of peaks appearing in the mass spectrum to a stored list of m/z values corresponding to ions of the labeled peptides to determine whether any of the peaks match (i.e., fall within a mass window surrounding) values on the stored list, step 240. An example of a table containing a stored list of m/z values, and their corresponding peptide sequences and charge states, is depicted in FIG. 3. The mass window used for matching peaks to values in the stored list may be set, either manually or automatically, in view of the mass accuracy of the mass analyzer as well as a desired degree of selectivity (i.e., the mass window may be set to a particularly narrow range to minimize spurious identifications arising from interfering ions having m/z values close to those of the labeled peptide ions). In certain embodiments, the stored list may be dynamically adjusted to account for expected elution times, i.e., at a particular moment in chromatographic time, the list may include the m/z values of only those labeled peptides that would be expected to be within their chromatographic elution window. In order to further avoid spurious identification, additional criteria may be applied to assess whether a labeled peptide ion is genuinely present; such criteria may include, for example, the presence/intensity of peaks at other expected charge states of the labeled peptide ion.

If no precursor ion peaks are found in the mass spectrum that match values on the stored list and satisfy other (optional) criteria, indicating that no labeled peptides are eluting at that timepoint, the method reverts to step 230 for acquisition of another MS1 spectrum.

If it is determined in step 240 that a precursor ion peak in the MS1 spectrum matches a value on the stored list, then the method proceeds to step 250, whereby MS/MS analysis is conducted to identify the presence of a characteristic product ion or product ions generated by fragmentation of the labeled peptide ion. According to the example presented above, wherein IGDYAGIK (SEQ ID NO:1) is a peptide of interest, a precursor ion peak of sufficient intensity may be identified in the MS spectrum at an m/z of 422.7363, matching (i.e., within the specified mass window of) the value on the stored list (FIG. 3) corresponding to the labeled peptide IGDYAGIK* (SEQ ID NO:2). In step 240, the precursor ions at the matching m/z value are mass isolated (i.e., separated from ions of other masses) and subjected to controlled dissociation to yield product ions. In the FIG. 1 example, isolation of the precursor ions may be effected by setting the amplitudes of the RF and resolving DC voltages of QMF 150 to values that provide selective transmission of ions having masses lying within a narrow window of the theoretical mass of the labeled peptide ions. In an illustrative implementation, QMF 150 is tuned to selectively transmit precursor ions in a 0.7 m/z wide window centered on the m/z value of the isotopically labeled peptide precursor ion; in the foregoing example, the transmission window may be set to 422.7363±0.35 m/z. Alternatively, isolation may be performed in a quadrupole ion trap, e.g., second mass analyzer 180, by application of a notched broadband waveform. Following isolation, the precursor ions are dissociated (fragmented) to generate product ions. In one embodiment, dissociation of the precursor ions is achieved by the collisionally activated dissociation (CAD) technique, whereby the ions are collided at high energies with atoms or molecules of a collision gas, such as nitrogen or argon. CAD may be effected by accelerating a beam of precursor ions into gas-filled collision cell 160. In another implementation, collisionally activated dissociation may be performed by kinetically exciting precursor ions within a quadrupole ion trap via application of an excitation voltage to the trap electrodes.

In alternative embodiments, dissociation techniques other than CAD may be utilized for production of fragment ions. Such dissociation techniques include electron transfer dissociation (ETD), pulsed-q dissociation (PQD) and photodissociation.

The product ions resulting from isolation and fragmentation of the precursor ion are then mass analyzed to generate an MS/MS spectrum. In an illustrative embodiment, the MS/MS spectrum is acquired by performing an analytical scan in an ion trap mass analyzer, e.g., second mass analyzer 180. Utilization of an ion trap mass analyzer may be particularly advantageous due to its ability to acquire mass spectra rapidly and at high sensitivity. As is known in the art, an analytical scan may be effected in an ion trap mass analyzer by the resonant ejection method, wherein a resonant excitation voltage is applied to the ion trap electrodes which the main RF trapping voltage is ramped, such that ions come into resonance with the resonant excitation field and are ejected to a detector in order of their m/z's.

In order to minimize the duration of the analytical scan and thereby increase the overall acquisition rate, the RF voltage ramp may be limited to a narrow range centered around the value corresponding to the ejection voltage of the characteristic product ion. In the example described below, the characteristic product ion is the $y_1$ ion of the IGDYAGIK* (SEQ ID NO:2) precursor ion, having an m/z of 155.1, the scan range width may be limited to 2 m/z, extending between 154 and 156 m/z.

The MS/MS spectrum from step 250 may then be processed in step 260 to determine the presence/intensity of a peak corresponding to a characteristic product ion of the isotopically-labeled precursor ion. According to one implementation, the characteristic product ion is the $y_1$ ion. Per standard nomenclature in the mass spectrometry art, a $y_1$ ion is the C-terminal fragment ion containing a single amino acid produced by cleavage of a C—N bond in the peptide chain. It is noted that collisionally activated dissociation of peptide ions yields primarily y-type and b-type product ions (complementary N-terminal fragment ions produced by C—N bond cleavages). In accordance with the labeling scheme described above, wherein the isotopically-labeled peptides are metabolically labeled with heavy forms of C-terminal lysine or arginine, the $y_1$ ion will consist of protonated heavy forms of lysine (155.1 m/z) or arginine (185.1 m/z). For the IGDYAGIK* (SEQ ID NO:2) precursor ion presented above as an example, the $y_1$ ion constitutes protonated heavy lysine.

In a basic implementation, the determination in step 260 will involve determining whether a peak of sufficient intensity (i.e., above a threshold value) is present in the MS/MS spectrum within a specified window of the m/z value of the characteristic product ion (e.g., $y_1$) of the isotopically-labeled peptide; if no peak is present, or the peak intensity does not meet the threshold criteria, then it is determined that the characteristic product ion is not present. Other implementations may base the determination in step 260 on whether the multiplicative product of the intensities of the product ion peak in the MS/MS spectrum and the corresponding precursor ion peak in the MS1 spectrum exceed a threshold, or whether the ratio between the intensities of the product ion peak and the corresponding precursor peak meet a threshold value or are within a specified range of values. Still other implementations may determine whether the multiplicative product or summed intensities of two or more product ion peaks in the MS/MS spectrum exceed a threshold. While the $y_1$ ion of the labeled peptide is the characteristic product ion in the foregoing example, those skilled in the art will recognize that other fragments incorporating the isotopically labeled moiety (e.g., the labeled amino acid) may be employed as the characteristic product ion instead of or in conjunction with the $y_1$ ion.

It is possible that greater specificity may be achieved if the determination in step 260 involves processing of multiple peaks within the MS/MS spectrum to ascertain whether plural characteristic product ions are present, rather than limiting the determination to a single characteristic product ion, such as the $y_1$ ion. However, such enhanced specificity will come at a cost of more difficult and complex method setup (since multiple characteristic product ion m/z's will need to be determined and stored for each of the isotopically-labeled peptides added to the sample), as well as possibly requiring longer MS/MS scan times. For this reason, it may be particularly favorable to limit the number of characteristic product ions to one ion (e.g., the $y_1$ ion) or a small plurality (e.g., two or three) of product ions, such as the $y_1$ ion and one or two additional characteristic product ions).

If it is determined that there are no product ion peaks in the MS/MS spectrum that match the m/z value of the characteristic product ion, then the method returns to step 230 for acquisition of an MS1 spectrum.

If, however, the MS/MS spectrum exhibits a product ion peak of sufficient intensity at the value of the characteristic product ion, then the method proceeds to step 270, whereby MS/MS analysis is conducted to measure the intensity of a product ion peak produced by dissociation of the endogenous peptide precursor ion corresponding to the labeled peptide ion matched in the MS1 spectrum. In other implementations, step 270 may involve measuring the intensity of a plurality of characteristic product ions that are produced by dissociating the endogenous peptide. This measured intensity may be utilized to quantify the amount of the endogenous peptide ion, in the manner discussed below. According to one embodiment, the MS/MS spectrum for step 270 is acquired in an HRAM mass analyzer, such as an orbital electrostatic trap mass analyzer (e.g., in first mass analyzer 170). Isolation of the endogenous peptide precursor ion, which has a mass that is different from the corresponding labeled peptide ion by the number of isotopic substitutions, may be accomplished by operation of the quadrupole mass filter to selectively transmit ions within a range of m/z's occupied by the endogenous peptide precursor ion. Dissociation may be effected by fragmenting the endogenous peptide precursor ions by CAD in collision cell 160. The resultant product ions are mass analyzed to generate an MS/MS spectrum.

According to one embodiment, step 270 includes isolating and fragmenting ions matching the m/z's of both the endogenous peptide ion and its isotopically labeled peptide counterpart, and collectively mass analyzing the product ions of each. In the above-described example, in which the endogenous peptide of interest is IGDYAGIK (SEQ ID NO:1), precursor ions corresponding to both the IGDYAGIK (SEQ ID NO:1) (endogenous) and IGDYAGIK*(SEQ ID NO:2) (isotopically-labeled) may be isolated and fragmented. Isolation and fragmentation of the two sets of precursor ions may be done sequentially, with subsequent combination of the product ions before mass analysis; alternatively, the two sets of precursor ions may be co-isolated (e.g., via use of a multi-notch isolation waveform, or by using an isolation width sufficiently broad to include the m/z's of both species) and the co-isolated precursor ions may be fragmented at the concurrently. Alternatively isolation, fragmentation, and analysis of the two sets of precursor ions may be done sequentially, whereby we produce two spectra one containing fragment ions belonging to the endogenous peptide and the other containing fragment ions belonging to the isotopically-labeled species. In this manner, the MS/MS spectrum will include peaks corresponding to product ions of both the endogenous peptide ion and the corresponding isotopically-labeled peptide ion. Since the isotopically-labeled peptides are added to the sample in known quantities, this enables absolute quantitation of the endogenous peptide using the ratios of measured intensities of product ions in the MS/MS spectrum.

Following acquisition of the second MS/MS spectrum, comprising product ions of the endogenous peptide ion and (optionally) of the "heavy" isotopically-labeled peptide ion, the method may return to step 230 for acquisition of an MS1 survey spectrum. Alternatively, a positive determination of the presence of the characteristic product ion in step 260 may trigger the sequential execution of a number of MS/MS quantitation scans before returning to step 230. In either case, the data in the MS/MS spectra acquired in step 270 may be used for relative or absolute quantitation of the endogenous peptide of interest in accordance with established methods, e.g., by integration of peaks in the ion chromatograms corresponding to the product ion(s) of the endogenous peptide precursor ion and (optionally) of the isotopically-labeled peptide precursor ion. It is noted that quantification may be done using the intensity of the counterpart product ion used for confirmation of the presence of the isotopically-labeled peptide in step (i.e., the $y_1$ ion of the endogenous peptide precursor), or alternatively quantitation may be done using one or more other product ions, or a combination of the product ion used for confirmation and other product ions.

Figure 4:
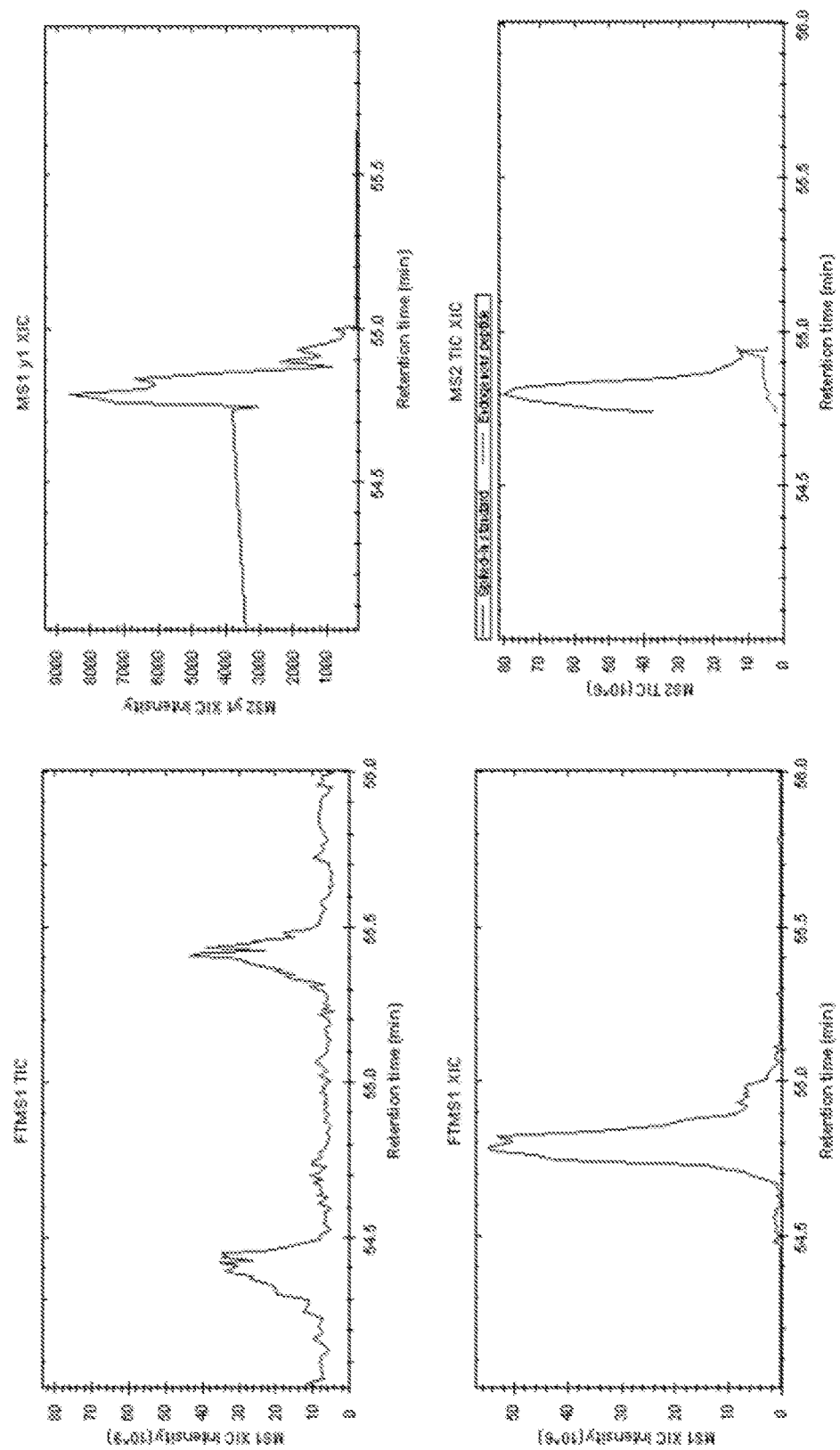
FIG. 4 depicts ion chromatograms corresponding to an isotopically-labeled peptide and its endogenous equivalent acquired using the FIG. 2 method.

FIG. 4 presents examples of ion chromatograms obtained using a specific implementation of the present method, in which a sample comprising 432 isotopically-labeled peptides spiked into lung cancer cell digests was analyzed. The ion chromatograms depict peaks corresponding to the isotopically-labeled peptide SFLLALPAPLVTPEASAEAR* (SEQ ID NO:6) and its endogenous counterpart SFLLALPAPLVTPEASAEAR (SEQ ID NO:5). The ion chromatogram in the lower left depicts, as a function of chromatographic retention time, the intensity of ions in the MS1 spectrum at the m/z of the SFLLALPAPLVTPEASAEAR* (SEQ ID NO: 6) precursor ion. It is observed that a peak is present centered approximately at the retention time of 54.8 minutes. The detection of precursor ions appearing in the spectrum at that m/z triggered MS/MS analysis of product ions, in accordance with the method described above. The ion chromatogram at upper right depicts the intensity of ions in the MS/MS spectrum at the m/z of the $y_1$ ion generated by dissociation of the SFLLALPAPLVTPEASAEAR* (SEQ ID NO:6) precursor ion (185.1 m/z). This chromatogram also exhibits a peak centered around 54.8 minutes), indicating a high likelihood that the detected precursor ion is in fact SFLLALPAPLVTPEASAEAR* (SEQ ID NO:6).

Per the present method, the detection of product ions having an m/z of the $y_1$ ion generated by dissociation of the SFLLALPAPLVTPEASAEAR* (SEQ ID NO:6) precursor ion, triggered acquisition of a second, high-resolution MS/MS spectrum (in the orbital trapping mass analyzer) for measurement of product ions of the endogenous SFLLALPAPLVTPEASAEAR (SEQ ID NO:5) peptide. The ion chromatogram at lower right depicts ion intensities at the m/z's of the $y_1$ product ions of both the endogenous SFLLALPAPLVTPEASAEAR (SEQ ID NO:5) peptide and its isotopically-labeled SFLLALPAPLVTPEASAEAR* (SEQ ID NO:6) counterpart. It can be discerned that peaks appear for both product ions, again centered around 54.8 minutes retention time, thereby enabling quantitation of the amount of the SFLLALPAPLVTPEASAEAR (SEQ ID NO:5) peptide in the sample.

While the foregoing examples describe a mass spectrometry method for use in the analysis of peptides in a sample, those skilled in the art will recognize that the method may be readily adapted to detect and measure other analytes, including substances of both biological and non-biological origins.

It is to be understood that while the invention has been described in conjunction with the detailed description thereof, the foregoing description is intended to illustrate and not limit the scope of the invention, which is defined by the scope of the appended claims.

What is claimed is:

1. A method for analyzing a peptide-containing sample by mass spectrometry, comprising:
   (a) preparing the sample for analysis, including adding a plurality of isotopically labeled peptides to the sample, each one of the isotopically labeled peptides producing, when ionized, a labeled peptide precursor ion of characteristic mass-to-charge (m/z) ratio;
   (b) chromotographically separating the sample;
   (c) ionizing the separated sample to generate sample ions;
   (d) performing an MS1 scan of the sample ions;
   (e) identifying a precursor ion in the MS1 scan that has a mass-to-charge ratio (m/z) matching an m/z of a labeled peptide precursor ion;
   (f) performing a first MS/MS analysis of the identified precursor ion to acquire a first MS/MS spectrum;
   (g) determining whether at least one peak is present in the first MS/MS spectrum matches one or more m/z's of a characteristic product ion or product ions generated by dissociation of the labeled peptide precursor ion; and
   (h) upon determination that the at least one peak is present in the first MS/MS spectrum, performing a second MS/MS analysis to measure an intensity of at least one product ion produced by dissociation of the endogenous peptide ion corresponding to the labeled precursor ion.

2. The method of claim 1, wherein steps (d) and (h) are performed in a first mass analyzer, and step (f) is performed in a second mass analyzer separate from the first mass analyzer.

3. The method of claim 2, wherein the first mass analyzer is an orbital electrostatic trap mass analyzer, and the second mass analyzer is a quadrupole ion trap mass analyzer.

4. The method of claim 2, wherein the second mass analyzer is a quadrupole mass filter.

5. The method of claim 1, wherein the at least one characteristic product ion is exactly one characteristic product ion.

6. The method of claim 5, wherein the one characteristic product ion is the $y_1$ product ion of the identified labeled peptide precursor ion.

7. The method of claim 1, wherein step (g) comprises determining whether the at least one peak has an intensity exceeding a threshold value.

8. The method of claim 1, wherein step (g) comprising determining whether the product of the intensity of the at least one peak and the measured intensity of the precursor ion measured in step (d) exceeds a threshold.

9. The method of claim 1, wherein step (g) comprises determining whether a ratio of the intensity of the at least one peak to the measured intensity of the precursor ion measured in step (d) is within a predetermined range of values.

10. The method of claim 1, wherein step (h) further comprises measuring an intensity of at least one product ion produced by dissociation of the identified precursor ion in a third MS/MS analysis.

11. The method of claim 10, wherein the product ion populations produced by the second and third MS/MS analyses are analyzed concurrently.

12. The method of claim 1, wherein step (f) is performed over a narrow m/z window in which the m/z of the at least one characteristic product ion is located.

13. The method of claim 1, wherein step (e) comprises determining whether an ion species present in a spectrum produced in the MS1 scan matches a value on a stored inclusion list.

14. The method of claim 13, wherein the stored inclusion list is adjusted based on chromatographic retention time.

15. The method of claim 1, further comprising:
   (i) quantifying the endogenous peptide based on a chromatogram corresponding to the measured intensities of the at least one product ion produced by dissociation of the endogenous peptide.

16. A mass spectrometer configured for mass analysis of a chromatographically separated sample containing a plurality of isotopically labeled peptides, comprising:
   an ion source for ionizing the sample to produce sample ions;
   a first mass analyzer;
   a second mass analyzer, separate and distinct from the first mass analyzer; and
   a controller, programmed with instructions for executing the steps of:
      (i) causing the first mass analyzer to perform an MS1 scan of the sample ions;
      (ii) identifying a labeled peptide precursor ion in the MS1 scan;
      (iii) causing the second mass analyzer to perform an MS/MS scan to measure an intensity of at least one characteristic product ion produced by dissociation of the identified labeled peptide precursor ion;
      (iv) determining whether the at least one characteristic product ion is present in the MS/MS scan; and
      (v) upon determination that the at least one characteristic product ion is present, causing the second mass analyzer to perform a second MS/MS scan to measure an intensity of at least one product ion produced by dissociation of the endogenous peptide ion corresponding to the identified labeled precursor ion.

\* \* \* \* \*

UNITED STATES PATENT AND TRADEMARK OFFICE
CERTIFICATE OF CORRECTION

PATENT NO. : 9,960,027 B2
APPLICATION NO. : 15/164113
DATED : May 1, 2018
INVENTOR(S) : McAlister et al.

Page 1 of 1

It is certified that error appears in the above-identified patent and that said Letters Patent is hereby corrected as shown below:

On the Title Page

Item [*]:
Delete "days" in Notice

In the Claims

Claim 1, Line 22:
Replace "chromotographically"
With --chromatographically--

Signed and Sealed this
Twelfth Day of November, 2019

Andrei Iancu
*Director of the United States Patent and Trademark Office*

SEQUENCE LISTING

```
<160> NUMBER OF SEQ ID NOS: 6

<210> SEQ ID NO 1
<211> LENGTH: 8
<212> TYPE: PRT
<213> ORGANISM: Saccharomyces cerevisiae

<400> SEQUENCE: 1

Ile Gly Asp Tyr Ala Gly Ile Lys
1               5

<210> SEQ ID NO 2
<211> LENGTH: 8
<212> TYPE: PRT
```

```
<213> ORGANISM: Artificial Sequence
<220> FEATURE:
<223> OTHER INFORMATION: IGDYAGIX, where Xaa represents the heavy (fully
      13C and 15N substituted) form of the terminal lysine amino acid,
      such that the isotopically-labeled version of the peptide has a
      mass 8 Dalton (Da) greater than the endogenous (light) peptide.
<220> FEATURE:
<221> NAME/KEY: MISC_FEATURE
<222> LOCATION: (8)..(8)
<223> OTHER INFORMATION: Isotopic enrichment of lysine (K) - the C and N
      elements making up the residue are enriched for heavy isotopic
      form

<400> SEQUENCE: 2

Ile Gly Asp Tyr Ala Gly Ile Xaa
1               5

<210> SEQ ID NO 3
<211> LENGTH: 10
<212> TYPE: PRT
<213> ORGANISM: Saccharomyces cerevisiae

<400> SEQUENCE: 3

Ser Ser Ala Ala Pro Pro Pro Pro Pro Arg
1               5                   10

<210> SEQ ID NO 4
<211> LENGTH: 10
<212> TYPE: PRT
<213> ORGANISM: Artificial Sequence
<220> FEATURE:
<223> OTHER INFORMATION: SSAAPPPPPX, where Xaa is the fully 13C and 15N
      substituted form of the terminal arginine amino acid, yielding an
      isotopically-labeled version of the peptide having a mass 10 Da
      greater than the endogenous (light) peptide.
<220> FEATURE:
<221> NAME/KEY: MISC_FEATURE
<222> LOCATION: (10)..(10)
<223> OTHER INFORMATION: Isotopic enrichment of arginine (R) - the C and
      N elements making up the residue are enriched for heavy isotopic
      form.

<400> SEQUENCE: 4

Ser Ser Ala Ala Pro Pro Pro Pro Pro Xaa
1               5                   10

<210> SEQ ID NO 5
<211> LENGTH: 20
<212> TYPE: PRT
<213> ORGANISM: Saccharomyces cerevisiae

<400> SEQUENCE: 5

Ser Phe Leu Leu Ala Leu Pro Ala Pro Leu Val Thr Pro Glu Ala Ser
1               5                   10                  15

Ala Glu Ala Arg
            20

<210> SEQ ID NO 6
<211> LENGTH: 20
<212> TYPE: PRT
<213> ORGANISM: Artificial Sequence
<220> FEATURE:
<223> OTHER INFORMATION: SFLLALPAPLVTPEASAEAX, where Xaa is the fully
      13C and 15N substituted form of the terminal arginine amino acid,
      yielding an isotopically-labeled version of the peptide having a
      mass 10 Da greater than the endogenous (light) peptide.
<220> FEATURE:
<221> NAME/KEY: MISC_FEATURE
<222> LOCATION: (20)..(20)
<223> OTHER INFORMATION: Isotopic enrichment of arginine (R) - the C and
```

-continued

```
    N elements making up the residue are enriched for heavy isotopic
    form.

<400> SEQUENCE: 6

Ser Phe Leu Leu Ala Leu Pro Ala Pro Leu Val Thr Pro Glu Ala Ser
1               5                   10                  15

Ala Glu Ala Xaa
            20
```